United States Patent [19]

Edwards

[11] Patent Number: 4,567,884

[45] Date of Patent: Feb. 4, 1986

[54] SPINAL HOOK

[76] Inventor: Charles C. Edwards, 3907 Greenway, Baltimore, Md. 21218

[21] Appl. No.: 446,001

[22] Filed: Dec. 1, 1982

[51] Int. Cl.[4] .............................................. A61F 5/04
[52] U.S. Cl. .................................. 128/69; 128/92 R; 128/92 B; 128/92 E; 128/92 A
[58] Field of Search ..................... 128/69, 92 R, 92 A, 128/92 B, 84 B, 92 E, 92 C, 303 R

[56] References Cited

U.S. PATENT DOCUMENTS

| | | | |
|---|---|---|---|
| 4,274,401 | 6/1981 | Miskew | 128/92 R |
| 4,382,438 | 5/1983 | Jacobs | 128/69 |
| 4,411,259 | 11/1983 | Drummond | 128/69 |

FOREIGN PATENT DOCUMENTS

| | | | |
|---|---|---|---|
| 2289164 | 5/1976 | France | 128/69 |
| 1241292 | 8/1971 | United Kingdom | 128/92 |

Primary Examiner—Richard J. Apley
Assistant Examiner—D. J. Isabella
Attorney, Agent, or Firm—Sherman and Shalloway

[57] ABSTRACT

This invention provides a spinal hook comprising a body having a rod receiving bore therethrough, a connecting portion and a shoe portion, the connecting portion extending along a plane approximately normal to the axis of the base and the shoe portion extending in a plane from the connecting portion and terminating in a tip on one end and joined to the connecting portion on the other end. Preferably, the side of the body facing the shoe portion has a convex curved outer surface to allow a closer fit to a vertebra to which the hook is attached. In preferred embodiments of the invention, the tip of the shoe is disposed closer to the body than the remainder of the shoe by either forming an acute angle between the shoe and the connecting portion or bending the tip of the shoe. The shoe may be tapered in both width and thickness and the connecting portion may be tapered in width from the body to the shoe to provide better fit between the hook and the vertebrae. The body is provided with one non-round slot or a plurality of holes on at least one side thereof to facilitate gripping and insertion of the hook. A holder adapted for use in connection with the present hook is also provided.

24 Claims, 12 Drawing Figures

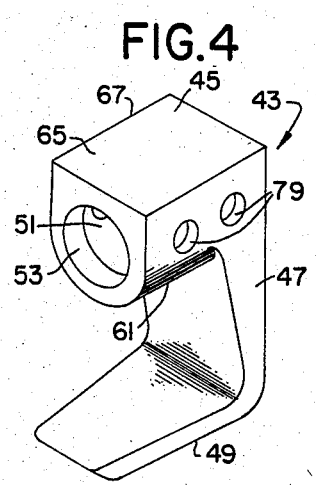
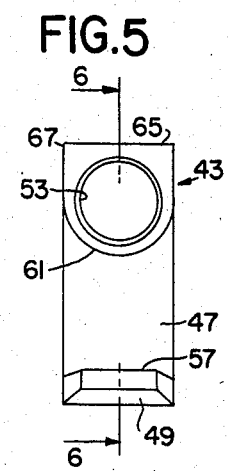
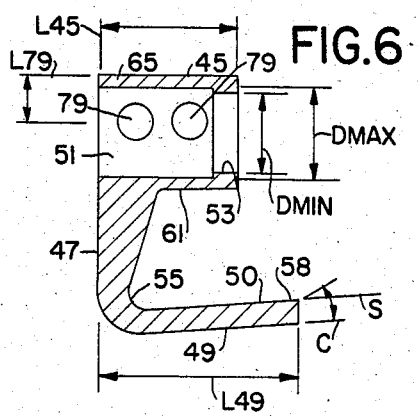
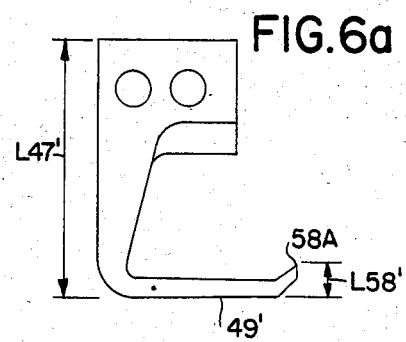
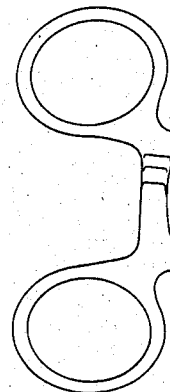
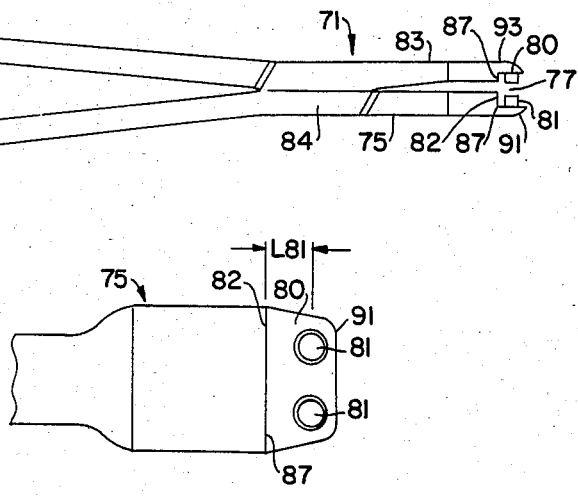

SPINAL HOOK

BACKGROUND OF THE INVENTION

1. Field of the Invention

This invention relates to spinal compression/distraction hooks of the type used in the Harrington TM system, wherein one or more rods are used to provide compressive or distractive force between pairs of hooks. The system was originally designed to be used to correct scoliotic deformities occurring in adolescent girls, but is now also used to correct other deformities and to repair or stabilize the spine following spinal fracture.

2. Description of Prior Art

The prior art includes a number of devices for use in correction of spinal deformities. These devices have been used primarily for the correction of lateral deviation of the spinal column, known as scoliosis. The spinal curvature which results from scoliosis is generally defined on the basis of specific reference points. In particular, the extreme upper and lower vertebrae and the most displaced vertebrae are of particular interest. The extreme upper and lower vertebrae are those which are the most inclined relative to the median longitudinal axis of the torso. The two planes within which the extreme upper and lower vertebrae can be found define the scoliotic angle. The most displaced, or apical, vertebra is defined as the vertebra which is the farthest from the median axis of the torso.

It is during surgery that the correction is completed and finalized. For this purpose, a solid rod with anchoring hooks is typically placed in the concavity of the curvature and a threaded rod with hooks is placed on the convexity of the curvature. These rods straighten the spine and maintain the correction until arthrodesis is attained by means of autogenous bone graft. The implants used most often to correct curvature during surgery are known as the Harrington TM distraction system and the Harrington TM compression system. (Harrington is a trademark of Zimmer, Inc., Warsaw, Ind.).

Another use for spinal rods is correction of kyphotic (hunchback) deformities produced by disease or spinal injury. In this use, either two compression or two distraction rods are used. Correction can be achieved by pushing the lamina of the apical vertebra anteriorly with the rods.

The shape and dimensions of existing spinal hooks (FIG. 1A) were generally designed for use on the above-mentioned treatment of scoliosis in adolescent girls. In this use, the hooks and rod act together like a jack to direct a longitudinal (uniplanar) force to elongate the spine and straighten the curvature. In recent years, however, surgeons have also begun treating fractured spines with the same hooks and rods. The typical patient with a fractured thoracic or lumbar spine is an adult male with thicker bones than the young girls for whom most spinal hooks were designed. Secondly, in treating fractured or dislocated spines, two rods rather than one are used. Accordingly, two hooks must be placed under the lamina of the top and bottom vertebral segment to be fixed with the rods.

All existing spinal hooks known to the inventor have four characteristics which make proper placement and implantation of the hooks unnecessarily difficult in many patients, (see FIG. 1A):

The rod housing or body is square. The corners of the anterior side of the hook body jam into the concavely shaped lamina/spinous process junction 95. This prevents the hook from seating fully and often makes it necessary for the surgeon to cut away bone to make space for the square hook body, using an osteotome.

The space between the hook body and shoe 96 is not wide enough to fit around the lumbar spine lamina for many adult patients.

When existing large hooks are placed on both the right and left lumbar lamina in the treatment of spinal injury, the existing broad and square hook shoes often bump into each other making proper seating of the hooks difficult or impossible. The hooks must then be overlapped at their shoes.

Existing hook designs offer either a broad, blunt shoe edge 97 or a sharp cutting shoe edge. Neither design is optimal for placement of distraction hooks in the thoracic spine. In the thoracic spine hooks wedge between two sides of facet joints 98. The edge of the blunt hook shoes are too thick, making insertion difficult. The sharp hook edge can cut into the bone causing a small fracture which can subsequently propagate resulting in hook dislodgement. The sharp edged hooks can also increase the chance of tearing epidural veins causing bleeding when used under either thoracic or lumbar lamina.

When these traction/distraction hooks are used to correct kyphotic deformity, the force exerted by the hook has a significant force vector in the posterior direction. (arrows in FIGS. 1A and 1B). Existing hooks are designed to exert force in the superior or inferior directions and are, therefore, prone to dislodgement when they are used to apply a force in the posterior direction.

Although postoperative hook dislodgement occurs following treatment of all spinal conditions, this problem is especially frequent when hooks and rods are used to correct kyphotic deformity where approximately 10%–15% of the patients have hooks dislodge postoperatively in the first month. Most fractures and dislocations of the thoracic or lumbar spine result in kyphotic deformity. Spinal hooks and rods are used to correct this deformity by combining distraction with 3-point loading of the spine. In this usage, the rod or more ideally, a rod-sleeve pushes forward over the apex of the kyphotic deformity and the hooks pull backwards or posteriorly. Such a sleeve is described in the inventor's U.S. patent specification Ser. No. 159,396 (June 13, 1980), which is hereby incorporated by reference. All existing hook designs known to the inventor feature a large (greater than 5 mm) hook radius. In almost all hooks for use in the thoracic or lumbar spine, portion 96 of the hook between the body and the tip of the shoe is rounded, usually semicircular with a constant radius. To the contrary, the shape of the undersurface of thoracic lamina 99 is essentially flat or slightly concave. Hence, the sole point of contact between the hook and thoracic lamina is at the very edge of the lamina. Particularly when the hook is used to effect a posteriorly directed force to correct kyphotic deformity, a moment is produced within both the hook and the lamina. The hook is pulling the inferior edge of the lamina posteriorly which causes it to tilt. Likewise, since the lamina is making contact with the curved inner aspect of the hook, the hook tilts in the same direction as the lamina. The curved hook then acts as a skid to encourage outward migration of itself relative to the lamina. When the lamina and hook are tilted and the patient bends forward and rotates slightly the hook can dislodge from under the thoracic lamina. In other words, the circular shape of the inner aspect of the hook shoe actually encourages dislodgement from under the thoracic lamina and facets.

The majority of the length of shoes on existing hooks is part of the hook's interior circular radius and, accordingly diverges from the hook body. As a result, the further the hook is advanced onto the flat underedge of the lamina, the further hook shoe tip 97 projects inwardly (or anteriorly) away from the lamina and into the spinal canal. This can be disadvantageous particularly for the spine-injured patient whose spinal cord 100 may be swollen and whose spinal canal may be already narrowed from fractured vertebral body fragments. Any forward tilting of the hook, as described previously, makes the hook shoe project yet further into the spinal canal.

Generally speaking, all previous hooks of which the inventor is aware were designed to direct only longitudinal (compression or distraction) forces against the spine, as opposed to hooks designed to also transmit forces directed posteriorly at approximately at 90° angle to the longitudinal axis of the spine.

There are Harrington TM hooks available which have hook shoes extending beyond the rod-engaging body of the hook, for example Zimmer TM No. 1279-01 Leatherman Hook TM. These hooks do not, however, exhibit a hook shoe which is angled inwardly with respect to the body or possess a narrow radius between the connecting portion and the shoe.

There are several difficulties frequently encountered with existing hooks holders. These include:
Excessive wobble between the holder and hook.
Impingement of the holder on laminar bone.
An uncomfortable handle.
A handle length similar to that of the rod holder.
Difficulty in aligning the holder.

All existing spinal hooks attach to the hook holder by means of a single pair of holes 101 in the hook in FIG. 1A which articulate with a pair of nipples on the hook holder. Since the nipples are opposite each other, they have the same axis of rotation. Existing hook holders also press against the top of the hook body to limit rotation about the nipples.

Particularly, when treating kyphotic deformity and spinal injury, corrective forces are applied to the spine manually by means of the hook holder attached to the spinal hook. Considerable force is often required for these maneuvers. As a result, the hook holder nipples wear away and the hook holder develops excessive "play." This results in excessive wobble between the hook holder and the hook. Because of the excessive wobble, the hook holder tilts and often bumps into the rod holder during the process of hook/rod engagement. Worse yet, the hook holder not infrequently breaks loose of the hook when corrective forces are being applied to the spine via the hook holder.

Another problem with existing hook holders is that the working end of the instrument is essentially square. This square edge at the lower end of the holder often abuts the junction between the lamina and spinous process bone 95 making it difficult to engage the hook holder with the hook once the hook is implanted under the lamina. Another minor disadvantage with existing hook holders is that there is no way to determine correct placement of the holder on the hook when attempting to articulate the two devices.

In the installation of a spinal hook system when repairing kyphotic deformities, two hook holders and one rod holder are used to grip a pair of distraction hooks and a rod. The unratcheted end of the rod is usually inserted into the inferior hook, after the ratcheted end of the rod has been first inserted into the superior hook. The rod is gripped near the inferior end, causing the rod holder to be close to the inferior hook holder. In inserting the rod into the inferior hook, the inferior hook is pulled posteriorly and a torque is applied to the hook by simultaneously pulling the inferior hook holder's handles superiorly. When the hook holder develops free play, it tends to pivot close enough to the rod holder to interfere with the rod holder at the handles. Since as much as 40 kg force is being applied in this procedure, the interference can raise significant problems for the surgeon and his assistants. There is presently no hook and rod attachment system tool set which avoids the above problem of hook interference.

SUMMARY OF THE INVENTION

It is, accordingly, an object of the invention to provide a spinal hook which is more anatomically suited for use in supporting the adult spinal column. More specifically, an object of the invention is to reduce the amount of time and trauma necessary to install the hook onto the spine and to provide a hook edge which enables the hook to wedge between two sides of facet joints in the thoracic spine without being so sharp as to cause trauma to the vertebrae or adjacent tissues. It is a further object to provide a hook which minimizes the penetration of the hook shoe into the spinal canal.

It is a further object to provide a spinal hook which minimizes its tendency to become dislodged post-operatively, particularly in cases in which the hook applies a significant vector of force to the spine normal to the longitudinal axis of the rod to which a hook is attached, and especially when the force vector is directed posteriorly away from the spinal vertebrae. This is particularly important in the correction of kyphotic deformities involving a three-point loading of the spine. It is a further object to provide a hook which minimizes hook-shoe projection into the patient's spinal canal under either a 3-point or uniplanar loading.

It is a further object of the invention to provide a means to more stably grip a spinal hook during surgery. On this point, it is an object to prevent excessive wobble and to provide a hook which meets with a tool in such a way as to avoid a tendency for the hook to tilt when being gripped by the tool.

Accordingly, a hook designed to secure a compression or distraction rod is provided in which the radius of curvature 55 between the connecting portion and shoe is reduced and in which the part of the hook secured to the rod has a convex, curved surface 61 facing the shoe in order to maximize clearance for the adjacent vertebral lamina. The hook is formed with a shoe tip which is closer to the body of the hook than any part of the hook shoe so as to further retard the hook's tendency to dislodge from the spine and to reduce the projection of the hook shoe into the spinal canal. In reducing the tendency of the hook to traumatize the spinal tissue, especially when being inserted at the facet of a vertebra, the hook design offers an edge which has a semi-sharp tip which is tapered in both dimensions.

In a further aspect of the invention, the hook is provided with two gripping dimples or holes on one or both sides of its body which mate with corresponding pins on a gripping tool. While the specific configuration of the gripping arrangement may vary, the configuration prevents the hook from pivoting with respect to the gripping tool. Further refinements of the gripping tool include a visual alignment of the hook with the tool's "business end" and a tapering distal end on the tool to provide increased clearance for the tool when the hook is being installed on the spine.

BRIEF DESCRIPTION OF THE DRAWINGS

FIG. 4 is an isometric elevation of a hook according to the invention.

FIG. 5 is an end view of the hook of FIG. 4.

FIG. 6 is a cross-section of the hook of FIGS. 4 and 5, taken along section 6—6 of FIG. 5.

FIG. 6A shows the side view of one embodiment of the present hook.

FIG. 7 shows bone-gripping forceps according to the invention.

FIG. 8 is a partial view of the forceps of FIG. 7, taken along line 8—8 of FIG. 7.

DESCRIPTION OF THE PREFERRED EMBODIMENTS

Figure 1:
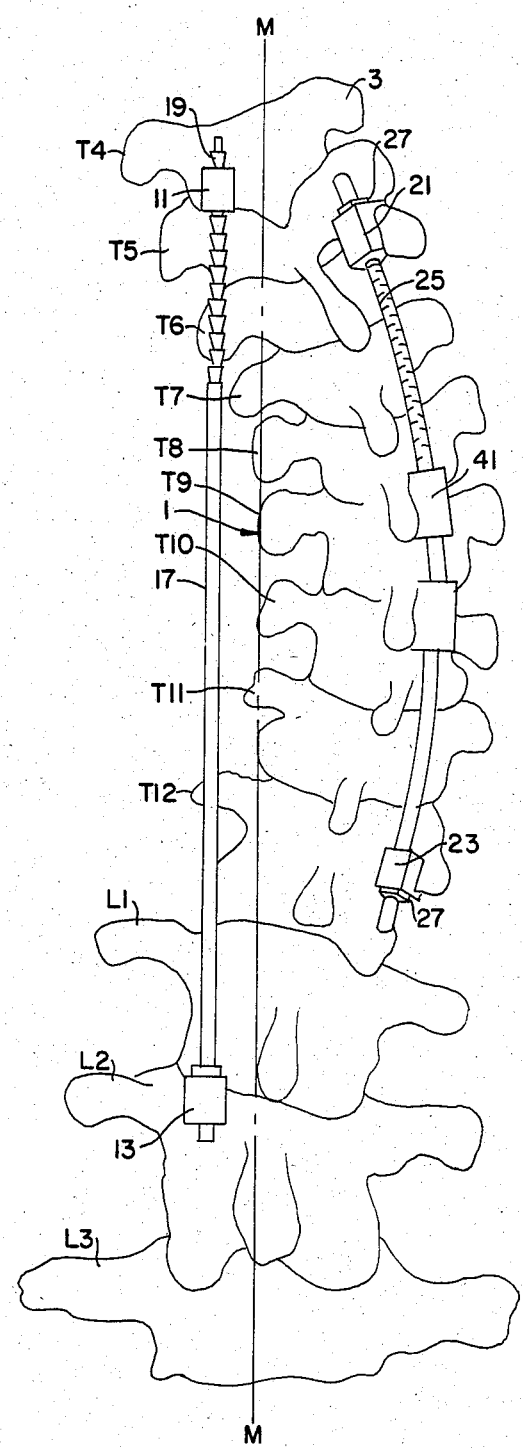
FIG. 1 shows a spinal rod and hook system installed on the posterior of a patient's spine.

FIG. 1 is an illustration of a spine of a patient suffering from scoliosis schematically represented from the rear. The spinal column 1 consists of vertebrae 3, including the vertebrae 3' designated T1–T12 and L1–L5 (of which T4–T11 and L1–L3 are shown). The patient illustrated in FIG. 1 exhibits a scoliosis involving a deviation of the vertebrae 3 to the right. The scoliotic curvature can be defined on the basis of the top vertebra T5 and the bottom vertebra T12 of the deviation, and the vertebrae T8 and T9 which are located at the peak of the curvature. It is noted that the vertebrae T5 and T12 are those which are most strongly inclined relative to the mediar longitudinal axis M—M of the body, while vertebrae T8 and T9 are those which are farthest from that axis. When the scoliotic curvature exceeds a given limit, it becomes necessary to consider surgical treatment of the scoliosis. The surgical treatment is known as arthrodesis and consists of fusing together the vertebrae of the scoliotic curvature, after correcting the scoliotic curvature to the maximum possible extent by straightening and opening. Such correction can be partially accomplished prior to the operation by continuous traction of the spine 1 or by corrective plaster casts.

However, it is during surgery that the correction is completed and finalized. Typically, a solid rod with hooks is placed in the concavity of the curvature, occasionally, a threaded rod with hooks is placed on the convexity of the curvature. These rods straighten the spine and maintain the correction until arthrodesis is attained by means of autogenous bone graft. The implants used most often to correct curvature during surgery are known as the Harrington ™ distraction system and the Harrington ™ compression system, illustrated in FIG. 1.

The distraction system of FIG. 1 includes two metallic anchoring devices 11 and 13 of the hook type, which are attached to selected ones of the vertebrae T4–T12 which comprise part of the spinal column 1. In distraction, the open ends of the hook are directed away from each other. A notched metal rod 17 serves as a stay and permits the spacing between the hooks 11 and 13. Such rods are available, for example from Zimmer, Inc. as Distraction Rods, catalogue Nos. 1250-00-01 through -25. One of the ends 19 of rod 17 is usually notched in such a manner as to provide a ratcheted adjustment of the distance between the hooks 11 and 13 by means of a spreading instrument. Generally, the superior anchoring device 11 is intended for fastening toward the upper end of the spine and is hooked onto a dorsal vertebra T4. Usually the hook of the superior anchoring device 11 is directed superiorly and shaped in such a manner as to permit its insertion between the spinous process and a transverse process of that vertebra, between the superior and inferior articular facets. The hook of the superior anchoring device 11 penetrates into the interarticular space and is supported on the vertebra T4.

Similarly, the inferior anchoring device hook 13 is intended to be fastened at the inferior end of the spine 1, and is often supported on a lumbar vertebra such as vertebra L2. It is contemplated that the hook 13 is directed inferiorly and supported on the lamina of the lumbar vertebra L2 between the spinous process and the articular facet mass.

The compression system consists of two or more metallic anchoring devices, hooks 21 and 23, which are attached to selected lamina or transverse processes of vertebrae T4–L2 which are situated on the convex side of the scoliotic curvature. In compression, the open ends of hooks 21 and 23 are directed towards each other. Threaded metal rod 25 serves as a stay or tension band between the hooks 21 and 23. Such rods are available from Zimmer, Inc., for example, as a Threaded Rod, catalogue No. 1257-00-10. Hooks 21 and 23 usually face each other and slide freely along threaded rod 25. These hooks 21, 23 are adjusted by means of hex nuts 27 so as to effect compression of the convexity of the scoliotic curvature. It is understood that more than two hooks and nuts can be used to achieve the desired amount of compression.

Additional straightening of both angular and rotary components of the scoliosis and improved fixation of the surgically implanted device is accomplished by the use of sleeve members 41. Prior to securing compression rod 25 in hooks 21, 23, sleeves 41 are fitted over the rod and spaced a distance apart selected by the physician. Once the rod is secured in the hooks 21, 23, with appropriate tightening, the sleeves can be adjusted up or down so that they can rest on and provide points of pressure application to correct angular and rotary deformity against the selected vertebrae. In the case of FIG. 1, sleeves 41 rest against and apply pressure to the surface of the spinous process of vertebrae T8 and T9.

Figure 2:
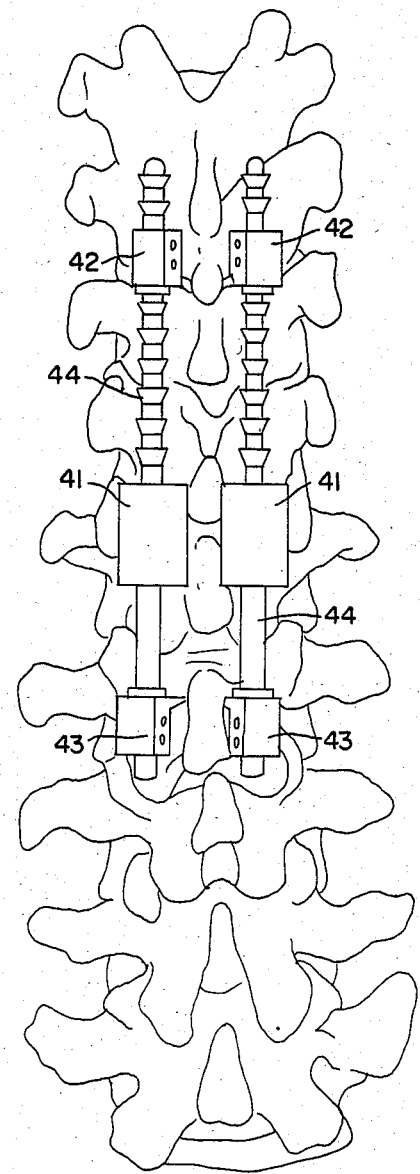
FIG. 2 is a posterior view of the rod and hook system according to the invention being used to correct a kyphotic deformity.
Figure 1A:
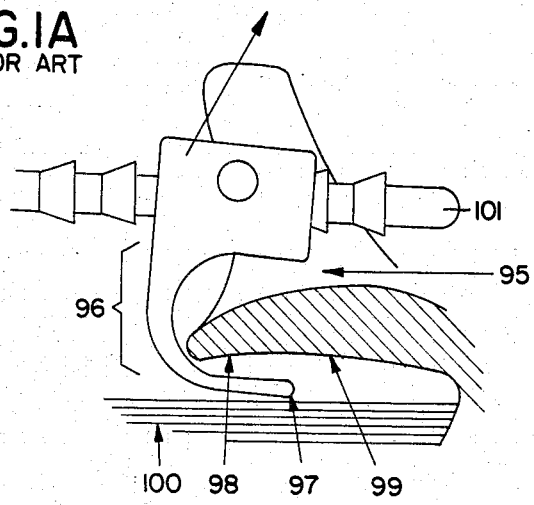
FIG. 1A shows existing standard hook (Zimmer cat. 1253) affixed to a mid-thoracic vertebral lamina with the force vector typically exerted on the hook in treating traumatic kyphosis.
Figure 3:
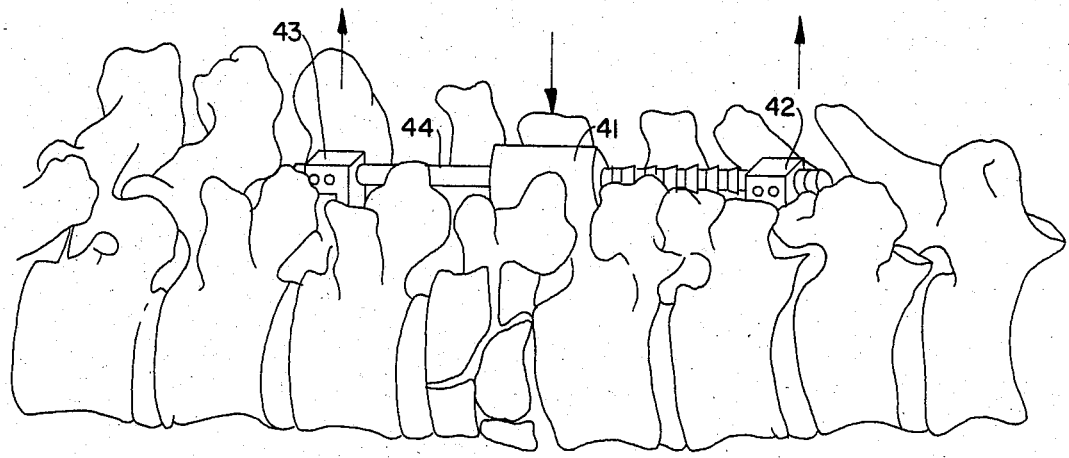
FIG. 3 is a right side view of the rod and hook system of FIG. 2, showing the forces applied by the system.

FIGS. 2 and 3 show the use of sleeves and rods in the correction of kyphotic deformity. The sleeves 41, in combination with the hooks 42, 43, effect a side loading of the rod 44 against the vertebrae. Since this side loading requires a minimum of three pressure points (two hooks and one sleeve). the system with the sleeve 41 is said to effect a three-point loading, as shown by the arrows in FIG. 3. In order to more soundly secure rods 25 and 44 to the vertebrae under three-point loading, the hooks 42 and 43 are contoured so as to prevent dislodgement from the vertebrae. FIGS. 4–6 show hook 43 which is is applied by a rod, formed so that it avoids dislodgement when the three-point force such as distraction rod 44, to the vertebrae. While the use of the hook 43 with distraction rod 44 is discussed, it is understood that inventive features also apply to hooks such as hooks 21 and 23 used with compression rods such as rod 25. The hook 43 comprises a body portion 45, a connecting horizontal portion 47 and a shoe portion 49, with the connecting portion 47 connecting the shoe portion 49 to the body portion 45. The present hook shown in FIG. 1B can be distinguished from the conventional hook FIG. 1A since body portion, connecting portion and shoe portion form distinct angular sections rather than one smooth continuous curved section as in the conventional hook. As a result, the present hook has a generally L-shaped configuration when viewed from its side. For simplicity of drawing, the connecting horizontal portion 47 is disposed vertically in FIGS. 4–6. It will, of course, be understood by those skilled in the art that, when installed with the Harrington ™ system, with the spine arranged vertically, the connecting horizontal portion 47 will, in fact, be horizontally disposed, as the connecting portion 47 extends in a plane anteriorly from the body portion 45.

The body portion 45 has a bore 51 therethrough which extends along the length of the body portion 45. The bore 51 is dimensioned so that the hook 43 may be placed over a Harrington ™ rod such as distraction rod 44. In the preferred embodiment, the minimum diameter $D_{min}$ can range between 6.40 and 6.53 mm. Most of the bore 51 has a larger diameter $D_{max}$ which preferably ranges from 6.86–7.126 mm. A ledge 53, defined by the change fro $D_{min}$ to $D_{max}$ forms a ratchet-type catch as has been developed by Paul Harrington for distraction hooks and remains typical of Harrington ™ distraction hooks.

As mentioned before, extending from the body 45 is a connecting portion 47 which connects to a shoe portion 49. The connecting portion 47 extends from the body 45 perpendicularly from the center axis of the bore 51 and from one end of the body 45. The connecting portion 47 joins the shoe portion 49 at a curve 55.

The shoe 49 terminates at a blunt edge 57 on the opposite side of the shoe 49 at the curve 55. This edge 57 is preferably formed by chamfering the shoe 49 from its exterior surface 59 at an angle c. Angle c is preferably about 30° from the exterior surface 59, although it could range from 15° to 60°. The resulting edge is then "broken" by polishing to form a blunt edge 57. The blunt edge 57 is able to wedge between two sides of facet joints in the thoracic vertebrae without being likely to cut into the bone.

It is important that the tip 58 of shoe portion 49 be disposed closer to the body portion 45 than the remainder of shoe portion 49. To accomplish this, shoe portion 49 can be angled inwardly towards the body portion 45 at an acute angle s with respect to the axis of the bore 51 (FIG. 6). Angle s is within the range of about 1° to 15° and preferably 5°. Alternatively, shoe portion 49 can be formed parallel to the body portion 45' with the end of the hook portion 49' being bent so that the tip 58A is situated closer to the body portion 45' (FIG. 6A). The distance ($L_{58}$) between tip 58A and the inside surface of the shoe 49' generally approximately 1 mm. By placing the tip 58 or 58A of hook portion 49 or 49' closer to body portion 45 or 45' and using an "L-shaped" hook, it has been found that dislodgement of the hook after implantation can be prevented.

Figure 1B:
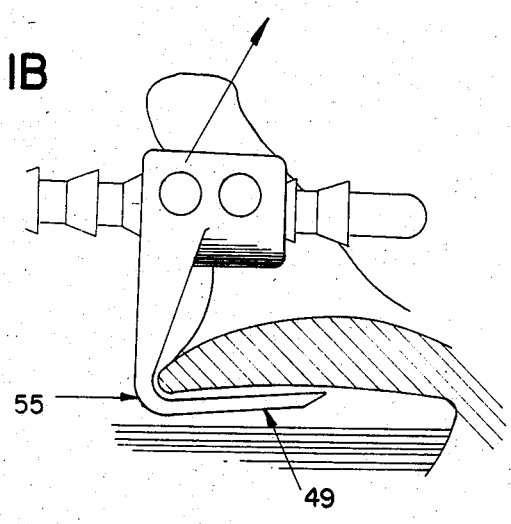
FIG. 1B shows the present hook affixed to the same lamina with the force vector typically exerted on the hook in treating traumatic kyphosis.

It has been found that the surface of the vertebral facet in the thoracic region of the spine is either vertical or slightly inclined posteriorly as viewed laterally. FIG. 1B shows that in the present invention, the "female" surface, i.e. the interior facing surface, of the hook fits more properly the shape of the thoracic lamina. Shoe portion 49 engages the vertebra at the blunt edge 57 or along most of the length of the shoe portion rather than at the curve 55. This avoids the tendency for the curve 55 (or radius 96) to act as an inclined plane to wedge the hook out of engagement with the vertebra when a significant vector of force is in the posterior direction as shown in both FIGS. 3 and 1A.

In order to further reduce the tendency for the curve 55 to wedge the hook out of engagement with the vertebra, the curve 55 is less than ⅓ the length of the connection portion 47 as measured from the point where curvate outer profile 61 of the body 45 meets the connecting portion 47 to the point on the exterior surface 59 of shoe portion 49 which has the greatest vertical distance from body portion 45. This reduces the inside radius of curve 55 to less than 4 mm and preferably less than 2.5 mm.

In the testing of prototypes of this hook configuration, it has been found that of 25 kyphotic spine-injured patients who had the hook installed in the thoracic or lumbar spine, none had the hooks dislodge. This preliminary result contrasts with a 10% to 15% dislodgement rate for conventional hooks during the first month.

When inserting a superiorly inclined hook such as hooks 11 or 42, a rod-like tool with a handle (not shown) is used to force the hook shoe 49 between the facets of adjacent vertebrae. By providing a chamfer from the exterior surface 59 at angle c, the insertion of the hook 42, which usually initially occurs at about a 10° angle from the eventual angle of placement, is facilitated. This is because the chamferred end of the shoe 49 at the edge 47 tends to, more-or-less, center the edge 57 between the vertebrae.

The connection portion 47 adjacent to the body 45 has a width which is substantially equal to that of the body 45. As the connection portion extends toward the shoe portion 49, its width decreases. This decrease in width continues through the shoe portion 49 until the shoe portion 49 terminates at the blunt edge 57. This is significant because, as shown in FIG. 2, in cases where more than one Harrington ™ system is used, it is possible that the inferior hooks 43 will be in close proximity to one another. In this way, the hooks are more narrow farthest away from the rods so that the shoe portions 49 are less likely to engage one another. This also simplifies positioning of the hooks 43 between the vertebrae.

The connecting portion has a thickness dimension measured parallel to the bore 51. The connecting portion tapers in its thickness from adjacent to the body portion 45 to the curve 55. That is to say, the connecting portion 47 is thickest (about 30 to 40% of the length of body 45) adjacent to the body portion 45 and thinnest near the curve 55. This encourages the hook 43 to move slightly in the direction of the blunt edge 57 when the hook 43 is pulled posteriorly to become fully seated under the lamina unlike existing hook (FIG. 1A) which backs out somewhat when loaded posteriorly. More importantly, when the hook is loaded in distraction or compression alone, the taper acts as an inclined plane to move the shoe posteriorly against the lamina, thus reducing the hook's displacement in the spinal canal and against spinal cord 100.

The body 45 of the hook 43 has a convexly curvate outer profile 61 at that portion of the body 45 which faces the shoe portion 49. The curvate outer profile 61 is generally coaxial with the bore 51 in order to provide a minimum of excess material at the profile 61 without compromising the strength of the body portion 45. The minimum of material is important because the curvate outer profile 61 is that part of the body portion 45 which is most likely to engage the concave vertebral lamina-spinous process junction 95. The curved contour of the outer profile 61 thus maximizes the clearance of the hook 43 with these vertebral elements for any given distance of the shoe portion 49 from the rod 44. This is particularly important in the case of inferiorly facing distraction hooks attached to lumbar vertebrae since the posterior surface of the lamina of these vertebrae is generally concave and abuts the squared-off edges of existing hook bodies. The curvate outer profile 61 also facilitates use of the rod and hook system with the 3-point loading sleeves 41 in that the rod 44 can be brought closer to the vertebrae. Significantly, it is important that a minimum of excision be made to the vertebrae in order to allow insertion of the hooks. By maximizing the clearance of the hooks, such as hook 13, the hook shoe can be fully seated around the lamina without removing any bone on the posterior surface of the lamina.

In order to further reduce the amount of cutting which may be necessary and in order to provide for better clearance of the installation of the hook 43, the body portion 45 is decreased in length. Referring to FIG. 6, the shoe portion 49 has a length $L_{49}$ which is dictated by the need to adequately engage a vertebra onto which the hook 43 is attached. The body portion 45, on the other hand, need not be as long as the shoe portion 49 and has a length $L_{45}$ which is appropriately shorter. In the preferred embodiment, if both $L_{45}$ and $L_{49}$ are measured from a back surface 63, $L_{45}$ would be at least 15 percent less than $L_{49}$. In the preferred embodiment, $L_{49}$ is approximately 15 mm and $L_{45}$ is approximately 11.5 mm, making the body 45 at least 2 mm shorter than the shoe portion 49.

Additional clearance for the lumbar vertebra is obtained by increasing the length of the connecting portion 47 to over 10 mm in order to increase the distance from the shoe 49 to the body beyond existing standard hooks. The increased length would not occur in hook 42 used with the thoracic vertebra, thereby bring the rod 44 closer to the patient's spine.

Additional strength for the body portion 45 is facilitated by providing an outside profile 65 of the body portion 45 as enlarged. As shown in FIGS. 5 and 6, the enlargement is accomplished by fabricating the outside profile 65 with squared off edges 67. It can thus be seen that the body portion 45 has the clearance fit advantages given by the curvate outer profile 61 along with the maximized strength of the squared-off outside profile. The squared-off edges 67 also facilitate the installation of the hook 43 with a hook holder as will be described.

In order to install the hooks such as hook 43, a specialized hook holder 71 is provided, as shown in FIG. 7. The hook holder 71 has a standard ratcheting forceps handle 73 and a gripping end 75 contoured to fit the hook 43. As shown in FIGS. 7 and 8, the gripping end 75 has a pair of recesses 77 which match the outside profile 65 of the body portion 45 of the hook 43. A pair of cross-bored holes 79 are drilled across the entire width of body portion 45 of the hook 43, as shown in FIG. 6. These holes 79 receive pins 81 (shown in FIGS. 7 and 8), with two pins 81 being located on each of a pair of scissors halves 83, 84 of the forceps 71. In another embodiment (not shown), two holes 79 are provided on only one side of the body portion 45 by drilling across one side of the body. Furthermore, it is not necessary that the holes 79 be drilled completely through the body portion 45 of the hook 43, but rather it is only necessary that the holes 79 be provided as dimples (not shown) on each side of the body portion 45. Alternatively, a non-round slot may be provided on at least one side of the body of the hook to facilitate gripping thereof.

Figure 9:
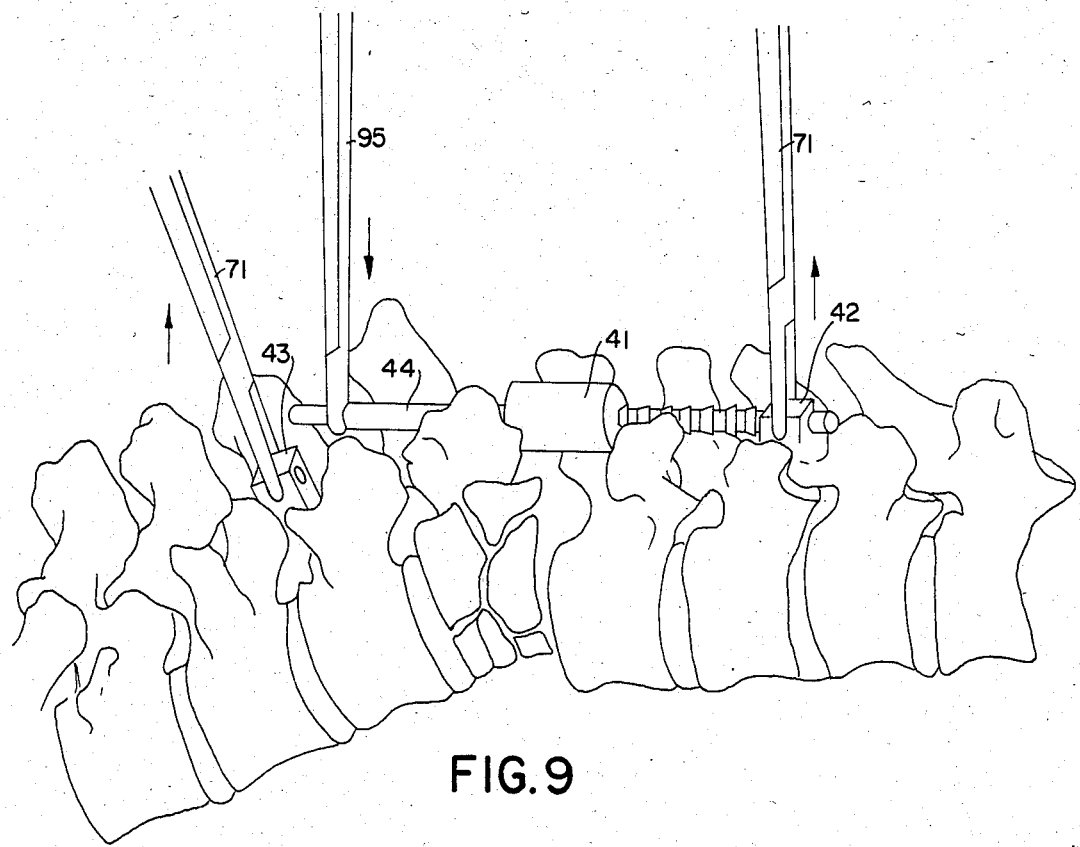
FIG. 9 shows the rod of FIGS. 2-3 being installed into a hook with the forceps of FIGS. 7-8.

Each recess 77 comprises a longitudinal wall 80 and lateral wall 82 which intersect at 90° to form a squared-off corner 87. The pins 81 are separated from the corner 87 by a distance $L_{81}$. This distance $L_{81}$ is equivalent to a distance $L_{79}$ from the holes 79 to the squared-off edges 67 as shown in FIG. 6. As a result of the equivalency of distances $L_{79}$ and $L_{81}$, the corners 87 on the holder 71 meet with the squared-off edges 67 on the hook 43. Furthermore, the combination of the pins 81 and the corner 87 provides increased stability over merely providing multiple pins 81 or merely providing one pin on each side of the hook holder along with the corner 87. In other words, stability is achieved both by the provision of four pins 81 and by the provision of the corners 87 to meet with squared-off edges 67. This increased stability allows the hook holder 71 to be used to exert various forces on the hook 43 to direct the hook 43 in various movements, particularly movements involving twisting of the hook 13 about an axis near the hook as shown in FIG. 9. In the preferred embodiment, the holes 79 in the hook 43 have center axes which are between 3.27 and 3.53 mm from the squaredoff edges 67. They have a diameter of between 3.3 and 3.5 mm. The pins 81 have center axes which are between 3.582 and 3.632 mm from the corners 87 and have diameters which are between 3.07 and 3.17 mm wide. This arrangement of hook holes and hook holder pins makes it possible for the present hook-holder to fit prior-art hooks and for prior art hook holders to fit the present hooks.

However, in order to prevent the physical dimensions of the gripping end 75 of the hook holder 71 from engaging vertebrae and thereby impeding its use, the gripping end 75 is tapered and rounded. Referring to FIG. 8, the outer tips 91 of the gripping end 75 are rounded. Also, the external surface 93 of the gripping ends are rounded (not shown). This increases access to the areas surrounded by spinal process in a manner similar to that provided by the tapering ends of needle nose pliers. To further reduce the liklihood of the hook holder from impinging on bone, the distance from the pins to edge 91 is less than that from the pins to edge 87.

Referring to FIG. 9, the sets of hooks 42, 43 and rod 44 of FIGS. 2–3 are installed by first installing the hooks as described supra, and then inserting the distraction rod 44 into the superior hook 42. Using a rod holder 95, the rod 44 is forced anteriorly downward at its inferior end while the inferior hook 43 is pulled upward, using hook holder 71. The hook holder 71 is also used to rotate the inferior hook 43 by force exerted in the superior direction on the handle 73 (not shown in FIG. 9), until the rod (44) can be advanced into the bore 51 of the inferior hook 43. The rod 44 is then ratcheted against the superior hook 42 and retained with a retaining ring (not shown) in the conventional manner.

As is clear from the above description, numerous changes can be made to the specific embodiments shown. For example, it is possible to provide holes 79 in pins 81 with spacing such that it is possible to engage a hook holder with a hook so that only a single pair of pins are engaged with the hook, thereby offsetting the hook holder with the hook if necessary. It is also possible to provide different configurations for the radiusing and angling of the various components of the hook. Furthermore, as described supra, the hook may be a compression hook such as hooks 21 and 23, rather than a distraction hook such as hooks 11, 13 and 43. The preferred dimensions of the hooks described are representative of the types of dimensions used in production and, as such, are not intended to be limitations. For this reason, the invention should be read as defined by the following claims.

1. A spinal hook for interengaging a rod in the human spine comprising a body which has a rod-receiving bore therethrough, a connecting portion and a shoe, the connecting portion extending along a plane approximately normal to the axis of the bore and joined with the body in a first joint and the shoe extending in a plane from the connecting portion terminating in a trip on one end and joined to the connecting portion in a second joint on the opposite end from the tip, the surface of the body facing the shoe having a rounded outside surface to avoid laminar impingement from hook body corners and to allow the body to fit closer to a vertebra to which the hook is attached and the top surface of the body being flat to allow secure articulation with a hook holding clamp.

2. The spinal hook of claim 1 wherein the second joint comprises a radiused joint, the radius of curvature thereof being less than ⅓ of the length of the connecting portion as measured from the point where the surface of the body facing the shoe meets the connecting portion of the exterior surface of the shoe.

3. The spinal hook of claim 1 wherein the shoe of the book ends in a tip which is angled with respect to the shoe member and disposed closer to the body than the shoe so that the tip contacts the undersurface of the thoracic facet or lamina when the hook is affixed to a patient.

4. Ths spinal hook of claim 1 wherein the second joint has an inside radius of curvature of less than 4 mm.

5. The spinal hook of claim 1 wherein the shoe portion forms an acute angle with the connection portion so that the tip of the shoe portion is closer to the center axis of the rod receiving bore than the second joint so that the tip contacts the undersurface of the thoracic vertebral facet or lamina when the hook is affixed to a patient.

6. The spinal hook of claim 5 wherein the shoe portion has a width along the longitudinal axis of the shoe portion which tapers to a reduced dimension from the second joint to the tip portion.

7. The spinal hook of claim 6 wherein the thickness of the tip portion of the shoe portion is tapered to a point which is rounded, thereby enabling the tip portion to be used to wedge between two sides of facet joints of thoracic vertebrae without being sharp enough to cut the bone or surrounding soft tissues.

8. The spinal hook of claim 7 wherein the connecting portion has a greater thickness at the first joint than at the second joint so as to define an inclined surface along the length of the connecting portion to facilitate intimate contact between the shoe and the undersurface of the lamina upon loading the hook.

9. The spinal hook of claim 8 wherein the length of the body of the hook, as measured along the axis of the bore, is at least 2 mm shorter than the length of the hook measured in the plane of the shoe from the tip or wherein the length of the body is less than 11.5 mm.

10. The spinal hook of claim 1 wherein the body has provided on at least one side thereof at least one non-round slot or a plurality of gripping holes designed to mate with corresponding locating pins on a gripping tool and the holes or slots having a configuration which prevents relative movement between the tool and the hook when the tool is gripping the hook.

11. The spinal hook of claim 10, wherein said configuration comprises holes or non-round slots arranged in pairs, one pair being located on a least one side of the body.

12. A set of at least two spinal hooks as defined in claim 1 wherein the connecting portion of one of the spinal hooks is longer than that of the other spinal hook so as to enable said one spinal hook to be placed on a lumbar vertebra and said other spinal hook to be place on a thoracic vertebra, thereby placing the rod closer to the spine than would otherwise be possible without excising bone.

13. A spinal hook for interengaging a rod in the human spine comprising a body which has a rod receiving bore therethrough, a connecting portion and a shoe, the connecting portion extending along a plane approximately normal to the axis of the bore and joined with the body in a first joint, and the shoe portion extending in a plane from the connecting portion terminating in a tip on one end and joined to the connecting portion by a second joint on the opposite end from the trip, the second joint having a radius of curvature of less than ⅓ of the length of the connecting portion as measured from the point where the surface of the body facing the shoe portion meets the connecting portion to the exterior surface of the shoe portion.

14. A spinal hook for interengaging a rod in the human spine comprising a body which has a rod receiving bore therethrough, a connecting portion and a shoe, the connecting portion extending along a plane approximately normal to the axis of the bore and joined with the body in a first joint, and the shoe portion extending in a plane from the connecting portion terminating in a tip portion on one end and joined to the connecting portion by a second joint on the opposite end from the tip, the body having provided on at least one side thereof at least one non-round slot or a plurality of gripping holes designed to mate with corresponding locating pins on a gripping tool and the holes or slot having a configuration which prevents relative movement between the tool and the hook when the tool and the hook when the tool is gripping the hook.

15. A spinal hook for interengaging a rod in the human spine comprising a body which has a rod receiving bore therethrough, a connecting portion and a shoe, the connecting portion extending along a plane approximately normal to the axis of the bore and joined with the body in a first joint, and the shoe portion extending in a plane from the connecting portion terminating in a tip portion on one end and joined to the connecting portion by a second joint on the opposite end from the tip, the shoe portion having a width in its plane which tapers to a reduced dimension from the second joint to the tip portion.

16. The spinal hook of claim 1 designed for use on the adult lumbar spine in which the distance between the body and shoe portions exceeds 10 mm in order to provide adequate clearance for full seating of the hook in large patients.

17. A spinal hook for interengaging a rod in the human spine comprising a body which has a rod receiving bore therethrough, a connecting portion and a shoe, the connecting portion extending along a plane approximately normal to the axis of the bore and joined with the body in a first joint, and the shoe portion extending in a plane from the connecting portion terminating in a tip portion of one end and joined to the connecting portion by a second joint on the opposite end from the tip, the shoe portion forming an acute angle with the connecting portion so that the tip of the shoe is closer to the center axis of the rod receiving bore than the second joint so that the tip contacts the undersurface of the thoracic vertebral facet or lamina when the hook is affixed to a patient, the shoe portion being non-rotatable relative to the body.

18. The spinal hook of claim 17 wherein the surface of the body facing the shoe has a convex curved outer surface to allow the rod receiving bore to fit closer to a vertebra to which the hook is attached.

19. The spinal hook of claim 18 wherein the shoe portion has a width along the longitudinal axis of the shoe portion which tapers to a reduced dimension from the second joint to the tip portion.

20. The spinal hook of claim 19 wherein the connecting portion has a greater thickness at the first joint than at the second joint so as to define an inclined surface along the length of the connection portion to facilitate intimate contact between the shoe and the undersurface of the lamina upon loading the hook.

21. The spinal hook of claim 20 wherein the length of the body of the hook, as measured along the axis of the bore, is at least 2 mm shorter than the length of the hook measured in the plane of the shoe from the tip.

22. The spinal hook of claim 20 wherein the body has provided on a least one side thereof at least one non-round slot or a plurality of gripping holes designed to mate with corresponding locating pins on a gripping tool.

23. The spinal hook of claim 22 wherein the thickness of the tip of the shoe portion is tapered to a point which is rounded.

24. A spinal hook for interengaging a rod in the human spine comprising a body which has a rod-receiving bore therethrough, a connecting portion and a shoe, the connecting portion extending along a plane approximately normal to the axis of the bore and joined with the body in a first joint and the shoe extending in a plane from the connecting portion terminating in a tip on one end and joined to the connecting portion in a second joint on the opposite end from the tip, the second joint having a radius of curvature of less than $\frac{1}{8}$ of the length of the connecting portion as measured from the point where the surface of the body facing the shoe portion meets the connecting portion to the exterior surface of the shoe portion, the connecting portion having a greater thickness at the first joint than at the second joint so as to define an inclined surface along the length of the connecting portion to facilitate intimate contact between the shoe and the undersurface of the lamina upon loading the hook.

* * * * *

UNITED STATES PATENT AND TRADEMARK OFFICE
CERTIFICATE OF CORRECTION

PATENT NO.   :   4,567,884
DATED        :   February 4, 1986
INVENTOR(S)  :   CHARLES C. EDWARDS It is certified that error appears in the above-identified patent and that said Letters Patent is hereby corrected as shown below:

IN THE CLAIMS

Claim 3, line 2, (column 11, line 49),
              delete "book", insert --hook--.
        line 5, (column 11, line 52),
              after "thoracic", insert --vertebral--.

Claim 4, line 1, (column 11, line 54),
              delete "Ths", insert --The--.

Claim 10, line 1, (column 12, line 16),
              delete "claim 1", insert --claim 8--.

Claim 17, line 8, (column 13, line 21),
              delete "of", insert --on--.

Signed and Sealed this

Twenty-ninth Day of April 1986

[SEAL]

Attest:

DONALD J. QUIGG

Attesting Officer

Commissioner of Patents and Trademarks